United States Patent [19]

Webb et al.

[11] Patent Number: 4,676,241
[45] Date of Patent: Jun. 30, 1987

[54] VENTILATION TUBE SWIVEL

[75] Inventors: Richard E. Webb, San Antonio, Tex.; Charles S. L'Hommedieu, Oklahoma City, Okla.

[73] Assignee: W.L.G. Technology, Spring, Tex.

[21] Appl. No.: 820,684

[22] Filed: Jan. 21, 1986

Related U.S. Application Data

[63] Continuation-in-part of Ser. No. 570,997, Jan. 16, 1984, abandoned.

[51] Int. Cl.4 .................. A61M 16/00; A62B 9/00
[52] U.S. Cl. .................. 128/207.14; 128/207.18; 128/912; 604/280; 604/283; 285/168; 285/272
[58] Field of Search .................. 128/207.14, 207.15, 128/207.17, 207.18, 910, 912, 204.18; 64/280, 283, 284; 285/163, 168, 181, 184, 272

[56] References Cited

U.S. PATENT DOCUMENTS

| 142,879 | 9/1873 | Weaver | 285/168 |
|---|---|---|---|
| 2,820,651 | 1/1958 | Phillips | 128/204.18 |
| 3,443,788 | 5/1969 | Kopp et al. | 285/168 |
| 3,659,612 | 5/1972 | Shiley et al. | 128/207.15 |
| 3,670,726 | 6/1972 | Mahon et al. | 128/204.18 |
| 3,964,488 | 6/1976 | Ring et al. | 128/207.18 |
| 3,983,660 | 4/1976 | Eross | 285/272 |
| 4,240,417 | 12/1980 | Holever | 128/912 |
| 4,274,406 | 6/1981 | Bartholomew | 128/912 |
| 4,311,136 | 1/1982 | Weikl et al. | 604/284 |
| 4,351,328 | 2/1982 | Bodai | 128/207.15 |
| 4,369,991 | 1/1983 | Linder | 285/272 |
| 4,416,273 | 11/1983 | Grimes | 128/912 |
| 4,506,665 | 3/1985 | Andrews et al. | 128/912 |
| 4,521,038 | 6/1985 | Cevny | 128/204.18 |

OTHER PUBLICATIONS

"Anesthesia Apparatus and Accessories Catalog", Ohio Chemical Hospital Equipment and Medical Gases Catalogue Jul. 20, 1966, p. 44.
"Connector, Adapters and Valves", Foregger Hospital Equipment Catalogue, Apr. 23, 1975, pp. 2-3.

Primary Examiner—Henry J. Recla
Assistant Examiner—Karin M. Reichle
Attorney, Agent, or Firm—James E. Bradley

[57] ABSTRACT

A connector swivel for connecting between a supply tube and an endotracheal tube accommodates movement of the patient. The swivel connector has an angled central member, with the axes of its ends intersecting each other at an obtuse angle. The central member has end pieces rotatably connected to each end. One of the end pieces is also angled, with its axes intersecting at an obtuse angle. The other end piece is straight and cylindrical.

4 Claims, 5 Drawing Figures

4,676,241

VENTILATION TUBE SWIVEL

CROSS-REFERENCE TO RELATED APPLICATIONS

This application is a continuation-in-part of application Ser. No. 570,997, filed Jan. 16, 1984, now abandoned.

BACKGROUND OF THE INVENTION

1. Field of the Invention

This invention relates in general to medical equipment, and in particular to ventilation tubes, such as endotracheal and tracheostomy tubes.

2. Description of the Prior Art

Whenever hospital patients require mechanical ventilation, a ventilation tube delivers air or oxygen to the patient from a remote source. The end of the ventilation tube is either inserted into the patient's nostril, or an incision is made so that the tube may be inserted directly into the patient's trachea. If the patient moves, the tube may drag against sensitive tissue inside the patient's nostril or trachea, causing pain and injury.

One experimental ventilation tube, which somewhat alleviated this condition, had an angled central member inserted between the end of the ventilation tube and the air or oxygen source, near the patient. The angled central member was brass and had a threaded connection on each end. The angle in the central member eased the pressure some, but still did not allow the patient to move very much.

Swivel couplings are used in some types of medical equipment to allow rotational movement. For example, U.S. Pat. Nos. 4,416,273 and 4,240,417 show couplings for an endotracheal tube having swivel connectors on each end. In each of these patents the swivel coupling allows only rotational movement, with no axial translation.

SUMMARY OF THE INVENTION

A swivel connector is connected between the insert or endotrachael tube and the supply tube. The swivel connector includes an angled tubular central member. The central member has tubular ends, each of which has an axis that intersects the other at an obtuse angle. An end piece is rotatably coupled to each end of the central member. One of the end pieces is a straight cylindrical member. The other end piece is angled, also. It has an axis on each end that intersects the other at an obtuse angle. One of the end pieces is connected to the insert tube and the other is connected to the gas supply tube.

The swivel connections, the angled end piece and angled central member allow rotational and translational movement of the supply tube relative to the insert tube.

The above as well as additional objects, features, and advantages of the invention will become apparent in the following detailed description.

DESCRIPTION OF THE PREFERRED EMBODIMENT

Figure 1:
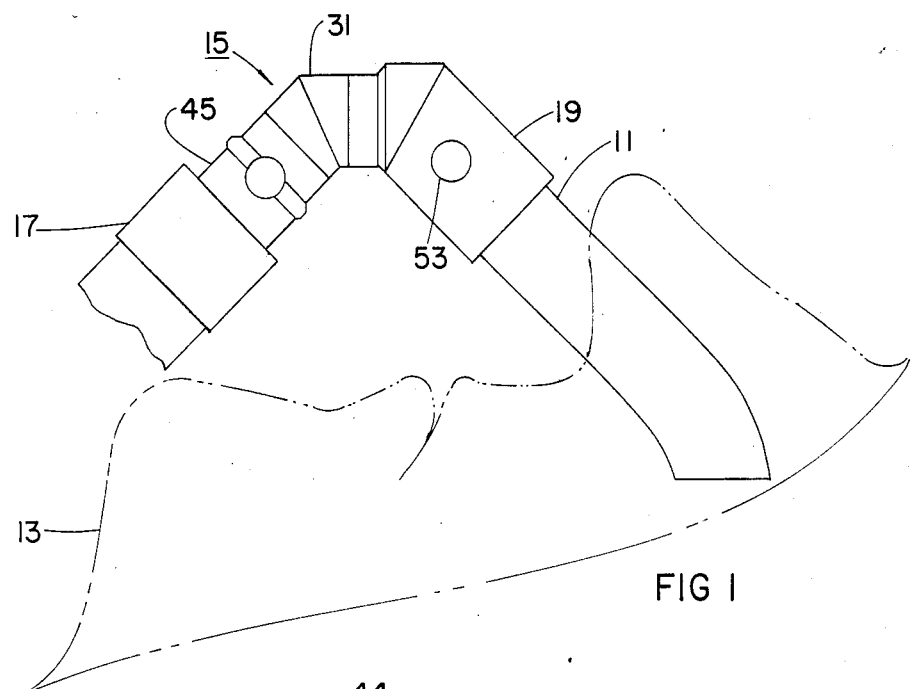
FIG. 1 is a side view of a ventilation tube connector connecting a supply tube to an endotraecheal tube inserted into a patient's nostril.

FIG. 1 illustrates an endotracheal or insert tube 11 inserted into the nostril of a patient 13. Insert tube 11 of this nature are also inserted into the trachea, with access provided through an incision made in the throat of the patient. Insert tube 11 is a flexible plastic member of conventional design.

Figure 2:
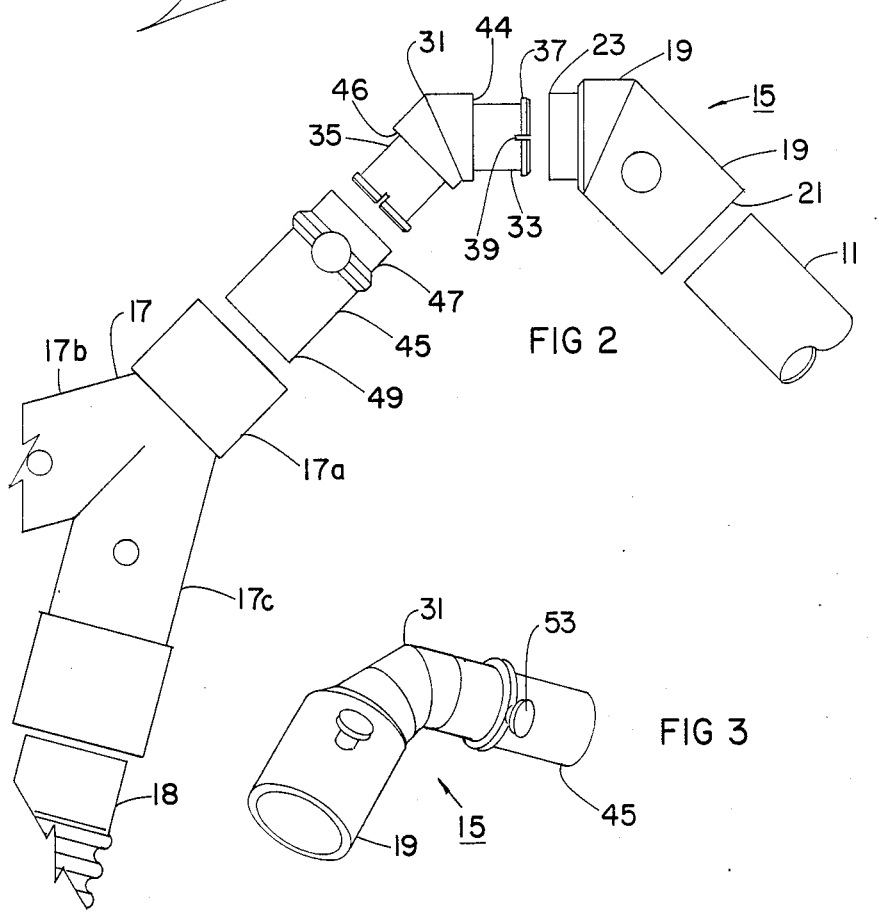
FIG. 2 is an exploded side view of the connector of FIG. 1.
Figure 3:
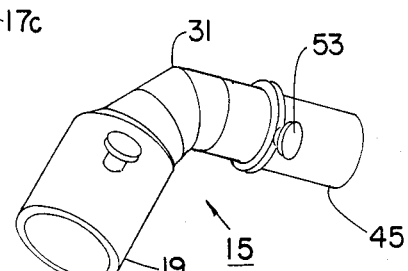
FIG. 3 is a perspective view of the connector of FIG. 1, with the endotracheal tube and the supply tube not being shown.

A resilient plastic swivel connector 15 is connected to the insert tube 11. Swivel connector 15 connects the insert tube 11 with a conventional supply tube adapter 17. Referring to FIG. 2, the supply tube adapter 17 has three tubular ends or ports. To facilitate the description herein, the term "inner" will refer to the direction toward the patient, while the term "outer" will refer to the opposite direction. The inner end 17a inserts tightly over the outer end of connector 15. The outer ends 17b and 17c each insert over a hose 18. One of the hoses 18 (only one shown) is connected to a supply source (not shown) for supplying gas for breathing. The other hose 18 allows the exhaust of gas from the patient's lungs. A valve mechanism (not shown) prevents flow from the supply source in one hose 18 from flowing through one end 17b or 17c and out the other end 17b or 17c to the other hose 18 to exhaust. Supply tube adapter 17 is a hollow plastic member, with each of the ends 17a, 17b, and 17c being in fluid communication with each other. The adapter 17 shown in the drawing has a Y configuration.

Figure 4:
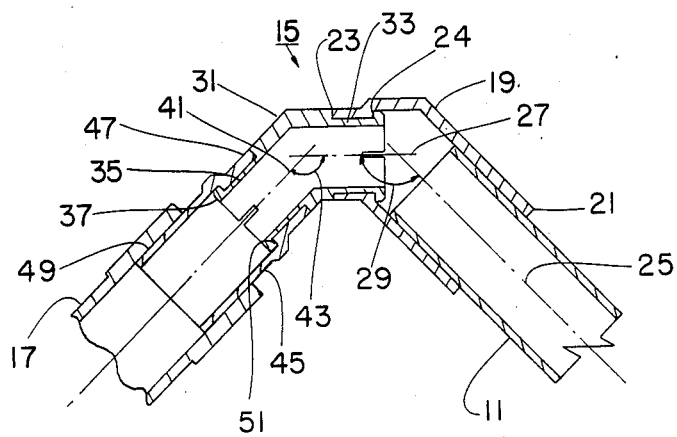
FIG. 4 is a vertical sectional view of the connector of FIG. 1, showing the connector in one position.

Referring to FIG. 4, the connector 15 includes a first tubular end piece 19. The end piece 19 has an inner end 21 that is a female tubular member. The first end piece 19 has an outer end 23 that is also tubular female member, but is of a smaller inner diameter than the inner end 21. This results in an internal shoulder 24 facing inwardly.

The inner end 21 is adapted to receive in tight frictional contact the outer end of the insert tube 11. The inner end 21 has a central axis 25 that will coincide with the axis of the insert tube 11 at the point where they connect. The first end piece 19 is angled, with the outer end 23 having a central axis 27 that intersects the axis 25 of the inner end 21. The intersection point occurs about one-third along the total length of the first end piece 19, and is closer to the outer end 23 then to the inner end 21. The angle 29 of intersection is obtuse, being greater than 90 degrees. Preferably, the angle 29 is 135 degrees.

Figure 5:
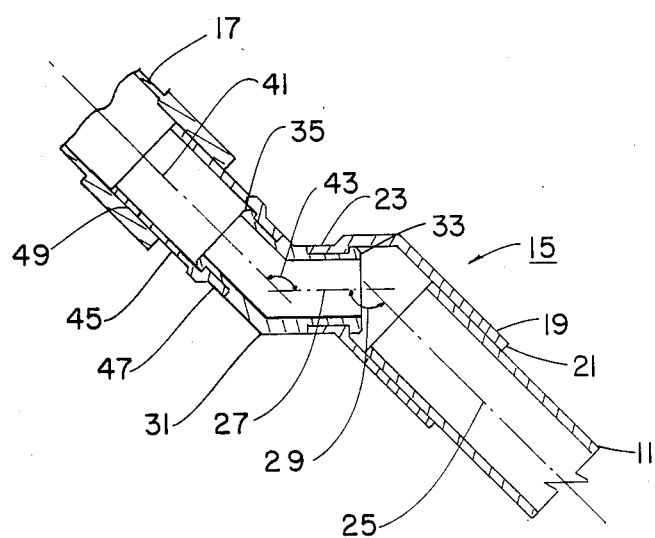
FIG. 5 is vertical sectional view of the connector of FIG. 1, showing the connector in another position.

Referring to FIGS. 2, 4 and 5, the swivel connector 15 also includes a tubular central member 31 that connects to the first end piece 19. The central member 31 is also an angled member, and has an inner end 33 and an outer end 35, both of which are male tubular members. Each end 33, 35 has a protuding rim 37 at the extreme end. Four slots 39 are cut into the sidewall of each end 33, 35, at the rim 37 to facilitate radial compression of the rim 37. The outer diameter of the inner end 33 is slightly less than the inner diameter of the outer end 23 of the first end piece 19. The rim 37 locates on the inner side of the internal shoulder 24 to retain the first end piece 19 and the central member 31 together.

The inner end 33 of the central member 31 has a central axis that is coaxial with the axis 27 of the outer end 23 of the first end piece 19, and thus not separately numbered. The outer end 35 of the central member 31 has a central axis 41 that intersects the axis 27 at an obtuse angle 43, being greater than 90 degrees. Preferably, the angle 43 is 135 degrees.

As shown in FIG. 2, the central member has a central portion of larger outer diameter than the reduced outer diameters of the ends 33 and 35. This results in oppositely facing external shoulders 44 and 46. Shoulder 44 contacts the edge of the outer end 23 of the first end piece 19.

A second end piece 45 is rotatably coupled to the outer end 35 of the central member 31. The second end piece 45 is a straight cylindrical member which has a central axis that is coaxial with axis 41 of the outer end 35 of the central member 31, and thus not separately numbered. This axis 41 also is coaxial with the axis of the supply tube adapter inner end 17a where it is joined to the second end piece 45. The second end piece 45 has a female inner end 47 and a male outer end 49. The inner end 47 is smaller in diameter than the outer end 49, resulting in an ouwardly facing internal shoulder 51. The rim 37 of the outer end 35 of the central member 31 locates outwardly of the internal shoulder 51 to retain the second end piece 45 on the central member 31. The inner diameter of the inner end 47 is slightly greater than the outer diameter of the central member outer end 35, providing a freely rotatable connection. The edge of the inner end 47 of the second end piece 45 abuts against the external shoulder 46 on the central member 31 for sliding contact.

The outer end 49 of the second end piece 45 is adapted to be pushed into the end 17a of the supply tube adapter 17, where it is retained by a frictional fit. Each of the first and second end pieces 19 and 45 have a pair of lugs 53 on each side to facilitate rotation and handling. The rotatable connections between the end pieces 19 and 45 with the central member 31 provide an unrestricted passage through the swivel connector 15. Also, the nonrotatable, friction fit connections of the insert tube 11 with the first end piece 19 and the supply tube adapter 17 with the second end piece 45, provide unrestricted passage of gas through the swivel connector 15. All of the connections are tight enough to form sufficient seals to withstand the normal pressures incurred for this type of apparatus.

The swivel connector 15 is assembled by pushing the end pieces 19 and 45 over the ends of the central member 31. The rims 37 will deflect during insertion due to the slots 39, but will snap into place against the internal shoulders 24 and 51. It will normally be preassembled prior to shipment.

To install the swivel connector 15, first the tube 11 will be inserted into the nostril of the patient or into the throat through an incision. The swivel connector 15 is connected to the insert tube 11 by pressing the end of the tube 11 into the first end piece 19 to form a tight frictional fit. The supply tube adapter 17 is connected to the swivel connector 15 by pressing its end 17a over the second end piece 45. Hoses 18 are inserted into the ends 17b and 17c of the supply adapter 17. This allows gas to be transmitted between the gas supply and exhaust hoses 18 and the patient 13.

The angled end piece 19 and angled central member 31, along with the rotatable connections, allow considerable movement of the hoses 18 relative to the insert tube 11. As shown by comparing FIGS. 4 and 5, in one position, the outer end 35 of the central member 31 is pointing downwardly with the axis 41 being perpendicular to the axis 25. If one rotates the central member 31 while holding the first end piece 19 stationary, the axis 41 will rotate in a conical path about its intersection with the axis 27. It would define a cone, with the apex of the cone being at the intersection of axis 27 with axis 41. When rotated 180 degrees from position shown in FIG. 4, the axis 41 will be parallel with the axis 25, but offset. While the central member 31 is rotated, the second end piece 45 is also allowed to rotate relative to the central member 31. The multiple positions between the two positions shown in FIG. 4 and FIG. 5 allow the patient 13 to move relative to the hoses 18 without painful movement of the insert tube 11.

The invention has significant advantages. The patient will be allowed to move his head and body without moving the insert tube relative to his throat, thus avoiding pain. The connector is simple and inexpensive to manufacture.

While the invention has been shown in only one of its forms, it should be apparent to those skilled in the art that it is not so limited, but is susceptible to various changes without departing from the scope of the invention.

We claim:

1. In a ventilation system of the type having an insert tube adapted for insertion into a breathing passage in a patient, a supply tube adapter of a type having one proximal and two distal tubular ends in fluid communication with each other, one of the distal ends being adapted to be connected to a source of gas, another of the distal ends being adapted to be connected to an exhaust hose, an improved connection means adapted to be releasably connected between the insert tube and the proximal end of the supply tube adapter, comprising in combination:

an angled tubular central member having a passage therethrough for the passage of gas, the central member having two tubular ends, each of which has a central axis, said central axes intersecting with each other at an obtuse angle;

a first tubular end piece having a passage therethrough for the passage of gas and only two tubular ends, the first tubular end piece having one of its tubular ends rotatably connected to one end of the central member for the passage of gas therebetween and the other of its tubular ends having means for releasable and frictional joining to the insert tube for the passage of gas therebetween, each end of the first tubular end piece having a central axis, said central axes in the first tubular end piece intersecting each other at an obtuse angle; and a second tubular end piece having a passage therethrough for the passage of gas, the second tubular end piece having one tubular end rotatably connected to the other end of the central member for the passage of gas therethrough and another tubular end having means for releasable and frictional joining to the proximal end of the supply tube adapter for the passage of gas therebetween;

the connection of the end pieces to the central member and the end pieces to the insert tube and supply tube adapter providing a continuous passage for the transmission of gas;

the rotatable connections of the tubular end pieces with the central member along with the intersecting central axes of the angled central member accommodating relative movement between the patient and insert tube and the supply tube adapter.

2. The system according to claim 1 wherein the second end piece is a straight cylindrical tubular member.

3. The system according to claim 1 wherein the sum of the two obtuse angles is substantially 270 degrees.

4. A ventilation tube system for a patient, comprising in combination:

an insert tube adapted to be inserted into a breathing passage of the patient;

a supply tube adapter having a proximal tubular end and two tubular distal ends in fluid communication with each other, one of the distal ends being adapted to be connected to a source of gas for supplying gas to the patient, the other of the distal ends being adapted to be connected to an exhaust hose for exhausting gas from the patient;

an angled tubular central member having a passage therethrough for the passage of gas, the central member having proximal and distal tubular ends, each of which has a central axis, said central axes intersecting with each other at an angle that is substantially 135 degrees;

a first tubular end piece having a passage therethrough for the passage of gas, the first end piece having only two tubular ends, one of the tubular ends being a distal tubular end which is inserted within and rotatably connected to the proximal end of the central member for the passage of gas therethrough, the other tubular end of the first end piece being a female tubular proximal end that receives therein in frictional contact one end of the insert tube for the passage of gas therethrough, each tubular end of the first end piece having a central axis, said central axes in the first end piece intersecting each other at an angle that is substantially 135 degrees, with the central axis of the distal end of the first end piece being coaxial with the central axis of the proximal end of the central member;

a second tubular end piece having a passage therethrough for the passage of gas, the second end piece having a proximal tubular end which is inserted within and rotatably connected to the distal end of the central member for the passage of gas therethrough the second end piece having a distal male tubular end which is inserted within and frictionally received by the proximal end of the supply tube adapter;

the second tubular end piece having a straight cylindrical configuration with a central axis that is coaxial with the central axis of the distal end of the central member;

the connection of the insert tube with the first end piece, the first end piece with the central member, the central member with the second end piece, and the second end piece with the supply tube adapter, providing a continuous passage for gas to and from the patient;

the rotatable connections and the angles of the first end piece and the central member allowing the distal end of the second end piece to rotate in a conical path with the apex of the cone at the intersection of the central axis of the second end piece with the central axis of the proximal end of the central member, the conical path defining one position wherein the central axis of the second end piece is perpendicular to the central axis of the proximal end of the first end piece, and another position wherein the central axis of the first end piece is parallel to the central axis of the proximal end of the first end piece, to accommodate relative movement between the patient and insert tube and supply tube adapter.

* * * * *